(12) United States Patent
Brockschmidt, Jr. et al.

(10) Patent No.: US 11,338,052 B2
(45) Date of Patent: May 24, 2022

(54) SINGLE-DIELECTRIC EXCIMER LAMP SYSTEMS AND METHODS

(71) Applicant: THE BOEING COMPANY, Chicago, IL (US)

(72) Inventors: Arthur Edward Brockschmidt, Jr., Renton, WA (US); Kevin S. Callahan, Everett, WA (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 17/352,796

(22) Filed: Jun. 21, 2021

(65) Prior Publication Data

US 2021/0393837 A1 Dec. 23, 2021

Related U.S. Application Data

(60) Provisional application No. 63/042,879, filed on Jun. 23, 2020.

(51) Int. Cl.
| | |
|---|---|
| *H01J 61/52* | (2006.01) |
| *A61L 2/26* | (2006.01) |
| *A61L 2/10* | (2006.01) |
| *H01J 61/30* | (2006.01) |
| *H01J 65/00* | (2006.01) |
| *B64D 11/00* | (2006.01) |

(52) U.S. Cl.
CPC .................... *A61L 2/26* (2013.01); *A61L 2/10* (2013.01); *H01J 61/302* (2013.01); *H01J 61/52* (2013.01); *H01J 65/00* (2013.01); *A61L 2202/11* (2013.01); *A61L 2202/25* (2013.01); *B64D 11/00* (2013.01)

(58) Field of Classification Search
CPC .... A61L 2/26; A61L 2/10; H01J 65/00; H01J 65/46; H01J 61/52
USPC .......................................................... 313/607
See application file for complete search history.

(56) References Cited

U.S. PATENT DOCUMENTS

| | | | | |
|---|---|---|---|---|
| 4,053,814 | A * | 10/1977 | Regan .................... | H05B 41/24 315/344 |
| 4,937,503 | A * | 6/1990 | Sigai ....................... | H01J 61/44 313/485 |
| 5,834,784 | A | 11/1998 | Morgan | |
| 2008/0264875 | A1* | 10/2008 | NeCamp ................. | C02F 1/325 210/748.11 |
| 2009/0101835 | A1 | 4/2009 | Fraser | |

(Continued)

FOREIGN PATENT DOCUMENTS

WO    WO-2019216485 A1 * 11/2019 ............. A61C 19/06

OTHER PUBLICATIONS

Extended European Search Report for EP 21181168.2-1212, dated Nov. 23, 2021.

*Primary Examiner* — Christopher M Raabe
(74) *Attorney, Agent, or Firm* — The Small Patent Law Group LLC; Joseph M. Butscher

(57) ABSTRACT

An excimer lamp includes a dielectric tube, an end cap, a conductive hollow tube, and an electrode grid. The dielectric tube has a closed end and an open end, and defines a cavity. The end cap sealingly covers the open end. The conductive hollow tube passes through the end cap and into the cavity of the dielectric tube, with a volume defined between an exterior surface of the conductive hollow tube and an interior surface of the dielectric tube. The volume is configured to hold a gas. The electrode grid is disposed on an exterior surface of the dielectric tube.

20 Claims, 8 Drawing Sheets

(56) References Cited

U.S. PATENT DOCUMENTS

| | | |
|---|---|---|
| 2010/0244688 A1 | 9/2010 | Braun |
| 2014/0087199 A1* | 3/2014 | Miura ........................ C08J 7/06 |
| | | 427/508 |
| 2014/0187116 A1* | 7/2014 | Doughty ................... H01J 9/34 |
| | | 445/38 |
| 2019/0096656 A1* | 3/2019 | Do ..................... H05B 41/2806 |

* cited by examiner

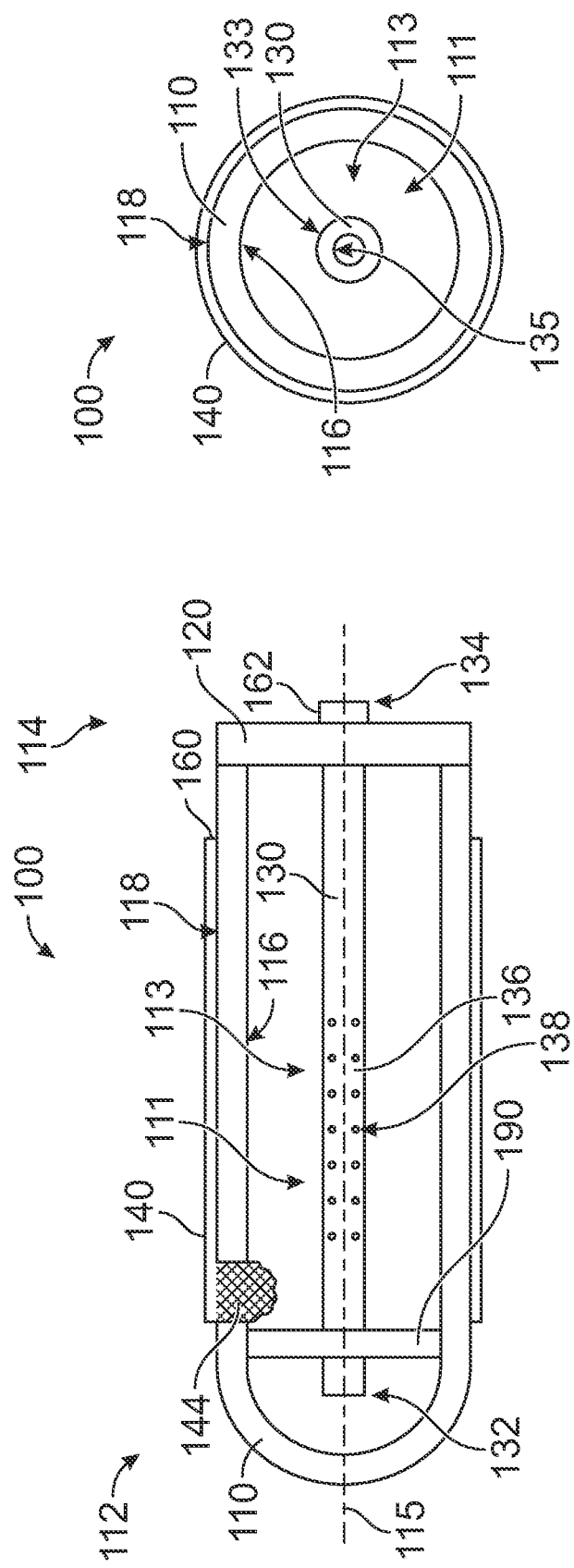

SINGLE-DIELECTRIC EXCIMER LAMP SYSTEMS AND METHODS

CROSS-REFERENCE TO RELATED APPLICATIONS

This application relates to and claims priority benefits from U.S. Provisional Patent Application No. 63/042,879, filed 23 Jun. 2020 and entitled "Single-Dielectric Excimer Lamp Systems And Methods," which is hereby incorporated by reference in its entirety.

FIELD OF THE DISCLOSURE

Embodiments of the present disclosure generally relate to excimer lamps (e.g., for sanitizing systems), such as may be used to sanitize structures and areas within vehicles or other enclosed spaces, and more particularly to systems and methods of providing such lamps having simplified manufacture and reduced cost to produce.

BACKGROUND OF THE DISCLOSURE

Vehicles such as commercial aircraft are used to transport passengers between various locations. Systems are currently being developed to disinfect or otherwise sanitize surfaces within aircraft, for example, that use ultraviolet (UV) light. UV light may also be used in other applications besides aircraft to disinfect or sanitize surfaces or objects.

For example, UV light around 222 nanometers wavelength may be utilized. However, known lamps that produce such wavelengths generally consist of two concentric quartz tubes, one positioned inside the other. Such lamps may operate at relatively high voltages and/or be costly or complicated to manufacture.

SUMMARY OF THE DISCLOSURE

A need exists for a system and a method for providing UV lamps for sanitizing that are easy to produce and use.

With those needs in mind, certain embodiments of the present disclosure provide an excimer lamp that includes a dielectric tube, an end cap, a conductive hollow tube, and an electrode grid. The dielectric tube has a closed end and an open end, and defines a cavity. The end cap sealingly covers the open end. The conductive hollow tube passes through the end cap and into the cavity of the dielectric tube, with a volume defined between an exterior surface of the conductive hollow tube and an interior surface of the dielectric tube. The volume is configured to hold a gas. The electrode grid is disposed on an exterior surface of the dielectric tube.

Certain embodiments of the present disclosure provide a method for assembling an excimer lamp. The method includes providing a dielectric tube having a closed end and an open end. The dielectric tube defines a cavity. The method also includes affixing an end cap to cover the open end. Further, the method includes introducing a conductive hollow tube into the cavity. The conductive hollow tube passes through the end cap and into the cavity of the dielectric tube. A volume is defined between an exterior surface of the conductive hollow tube and an interior surface of the dielectric tube. The method also includes disposing an electrode grid on an exterior surface of the dielectric tube. Also, the method includes introducing a gas into the volume.

BRIEF DESCRIPTION OF THE DRAWINGS

FIG. 1 illustrates a side schematic view of an excimer lamp, according to an embodiment of the present disclosure.

FIG. 2 illustrates an end sectional view of the excimer lamp of FIG. 1.

DETAILED DESCRIPTION OF THE DISCLOSURE

Figure 4:
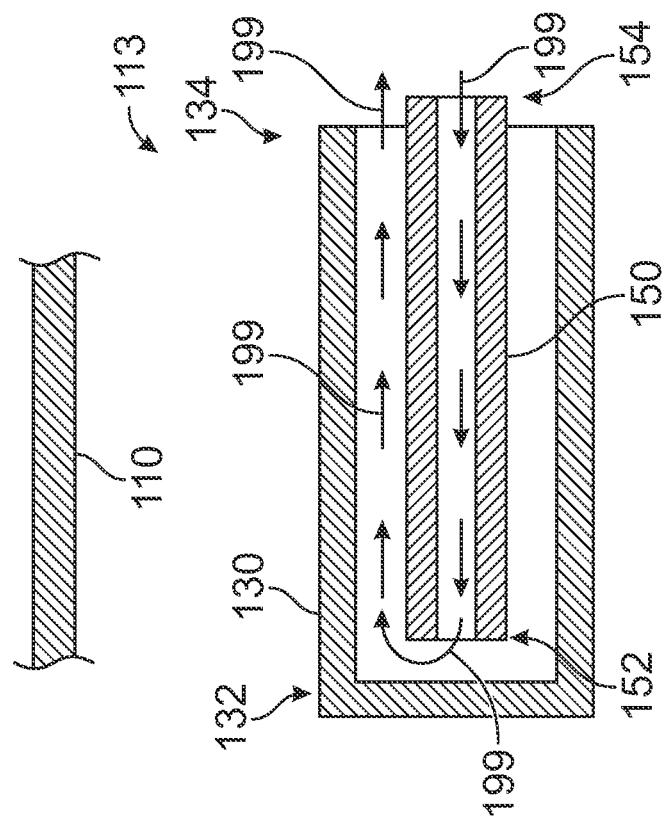
FIG. 4 illustrates a side view of the cooling tube of FIG. 3.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition can include additional elements not having that condition.

Certain embodiments of the present disclosure provide a 222 nm UV lamp that is easy to manufacture and convenient to use. For example, various embodiments provide a single dielectric excimer lamp that eliminates one of the glass layers of conventional lamps, and sealing an open end of a quartz tube with a metal cap (e.g., by brazing). The elimination of the glass layer reduces the voltage required to operate the lamp, as well as reduces the cost of production of the lamp. In various embodiments, excimer lamps as disclosed herein may be utilized in connection with portably UV wand systems, for example for use in the interior of an aircraft. Various embodiments may be configured for different sizes.

Various embodiments provide an excimer UV lamp and/or methods for making an excimer UV lamp. The lamp in various embodiments includes a quartz tube that is closed on one end, and has a metal cap or end piece that is brazed or welded to the other, open end to provide a seal (e.g., a hermetic seal) on the tube. The metal cap or end piece may be made with a material such as Kovar or other material that matches the thermal coefficient of expansion of quartz. The metal cap or end piece has an opening that allows a stainless tell tube to be inserted through the metal end piece, with the stainless steel tube extending into the inner chamber of the quartz tube. The stainless steel tube is welded or brazed to the metal cap or end piece. The stainless steel tube may be supported or held in place with a spacer (e.g., a doughnut shaped spacer). In various embodiments, the stainless steel tube is open initially on both ends at the time of assembly. The stainless steel tube is inserted into an opening of the spacer within the quartz tube, with the spacer resting against or abutting the inner surface of the quartz tube near the closed end of the quartz tube.

The excimer lamp also includes a conductive grid. In various embodiments, the conductive grid is formed as a part of the quartz tube, joined to the quartz tube, or otherwise disposed on an outer or exterior surface of the quartz tube. For example, a conductive mesh grid may be made of a woven metal textile of thin conductive wires that may be printed on the outer surface of the quartz tube. In some embodiments, a band pass filter may also be applied to the exterior surface of the quartz tube.

The stainless steel tube acts as an electrode. In some embodiments, the stainless steel tube is also used to vacuum fill the interior of the chamber with a gas (e.g., Krypton Chlorine gas). For example, a gas line may be attached to the open end of the stainless steel tube that projects out of the quartz tube, and gas introduced into the chamber via the stainless steel tube. Once the chamber has the desired amount of gas (e.g., a desired pressure has been reached), the open end of the stainless steel tube may be crimped or otherwise sealed to maintain the gas in the chamber. The electrodes (e.g., the conductive mesh grid and the stainless steel tube) may be coupled to an electrical source to operate the lamp. For example, a ground connector may be connected to the conductive mesh grid, and a high voltage lead from the power supply may be soldered or crimped onto the stainless steel tube.

In some embodiments, the stainless steel tube may have small holes through its wall in the portion positioned inside the quartz tube to facilitate gas flow within the chamber. Additionally or alternatively, in some embodiments, the excimer lap is adapted or configured to allow for flow of a cooling liquid through the stainless steel tube.

FIG. 1 illustrates a schematic side view of an excimer lamp 100, and FIG. 2 illustrates an end sectional view of the excimer lamp 100. As seen in FIGS. 1 and 2, the depicted example excimer lamp 100 includes a dielectric tube 110, an end cap 120, a conductive hollow tube 130, and an electrode grid 140. The illustrated example excimer lamp 100 also includes a spacer 190 that helps position and support the conductive hollow tube 130 inside the dielectric tube 110. Generally, a voltage is applied between the electrode grid 140 and the conductive hollow tube 130 to cause emission of UV light from a gas maintained in the dielectric tube 110.

The dielectric tube 110 has a closed end 112 and an open end 114 located on opposite ends of the dielectric tube 110. The dielectric tube 110 defines a cavity 111 between the closed end 112 and the open end 114. In the illustrated example, the dielectric tube 110 is cylindrically shaped or has a circular cross section, and extends along an axis 115. The dielectric tube 110 has an interior surface 116 oriented toward the inside of the dielectric tube 110 or toward the axis 115. The dielectric tube 110 also has exterior surface 118 that is oriented away from the inside of the dielectric tube 110 or away from the axis 115. The dielectric tube 110 in various embodiments is made of a transparent material, and has a sufficient thickness and dielectric properties for functioning of the excimer lamp 100. The dielectric tube 110 may be made of quartz glass, as one example, or may be made of fused silica glass, as another example.

The end cap 120 is joined to the dielectric tube 110 proximate the open end 114 of the dielectric tube 110. The depicted end cap 120 is joined to the dielectric tube 110 to sealingly cover the open end 114, to maintain gas within the dielectric tube 110 during operation of the excimer lamp 100. For example, the end cap 120 may be brazed to the dielectric tube to provide a seal. In the illustrated example, the end cap 120 is disc shaped to match the circular cross-section of the depicted dielectric tube 110. The end cap 120 may be made of a metal. In some embodiments, the end cap 120 has a thermal coefficient of expansion that corresponds to a thermal coefficient of expansion of the dielectric tube 110. For example, in some embodiments, the end cap 120 is made of a metal such as Kovar to match the thermal coefficient of expansion of a quartz tube.

The conductive hollow tube 130 passes through the end cap 120 and into the cavity 111 of the dielectric tube 110. The conductive hollow tube 130 is made of an electrically conductive material such as a metal, for example stainless steel. The conductive hollow tube 130 has a distal end 132 located in the interior of the dielectric tube 110 (or closer to the closed end 112) and proximal end 134 located outside of the dielectric tube 110 (or closer to the open 114). A seal is provided between the conductive hollow tube 130 and the end cap 120. For example, the end cap 120 in various embodiments has a pre-formed opening through which the distal end 132 of the conductive hollow tube 130 may be passed. Once the conductive hollow tube 130 is in a desired position, the hollow tube 130 may be sealingly coupled to the end cap 120, for example by brazing.

The conductive hollow tube 130 has an exterior surface 133 and an interior surface 135. A volume 113 is defined between the exterior surface 133 of the conductive hollow tube 130 and the interior surface 116 of the dielectric tube 110. The volume 113 is configured to hold a gas (e.g., Krypton Chlorine gas). In the illustrated example, the conductive hollow tube 130 has a circular cross-section like the dielectric tube 110, allowing for a uniform spacing between the conductive hollow tube 130 and the electrode grid 140 that is disposed on the dielectric tube 110.

In various embodiments, the conductive hollow tube 130 is closed on at least one end. For example, the conductive hollow tube 130 may be open at both ends at an initial time of assembly. After the conductive hollow tube 130 is joined to the end cap 120, the conductive hollow tube 130 may be used as a fill tube to supply gas to the volume 113. Once the gas has been supplied to the volume, the conductive hollow tube 130 may be closed (e.g. by crimping) at the proximal end 134 to prevent escape of the gas from the volume 113.

In some embodiments, the conductive hollow tube 130 comprises a body 136. The body 136 includes circulation holes 138 passing through the body 136 (e.g., in a direction substantially perpendicular to the axis 115). The circulation holes 138 allow gas to pass through the conductive hollow tube 130 during operation of the excimer lamp 100.

In some embodiments, as discussed herein (e.g., in connection with FIGS. 3-5), the conductive hollow tube 130 may be closed at the distal end 132 (e.g., to facilitate use of a cooling fluid flowing through the conductive hollow tube 130 while preventing mixing of the cooling fluid in the conductive hollow tube 130 and the gas in the volume 113). In such embodiments, a separate fill tube (not shown) may be used to fill the volume 113 with gas.

In some embodiments, the conductive hollow tube 130 is configured to allow passage of a cooling fluid. For example, the conductive hollow tube 130 may be coupled to a coolant source that supplies fluid to and removes fluid from the conductive hollow tube 130. The cooling fluid may be a liquid, or, as another example, air (e.g., ambient air). In some embodiments, a tube may be used within the conductive hollow tube to help provide and/or direct the flow of a cooling fluid within the conductive hollow tube 130. Use of cooling within the conductive hollow tube 130 (and accordingly within the dielectric tube 110) allows for cooling of the excimer lamp 100 without interruption or blocking of light emitted from the excimer lamp 100 that may be caused if an external cooling arrangement were utilized.

Figure 3:
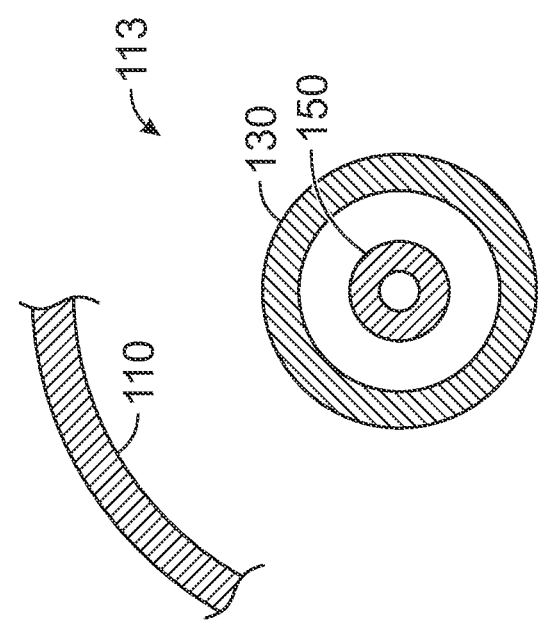
FIG. 3 illustrates an end sectional view of a cooling tube, according to an embodiment of the present disclosure.

FIG. 3 provides an end sectional view of a cooling tube 150 disposed within an example conductive hollow tube 130, and FIG. 4 provides a side sectional view of the cooling tube 150. In the example depicted in FIGS. 3 and 4, the cooling tube 150 is disposed within the conductive hollow tube 130. The distal end 132 of the conductive hollow tube 130 is closed to prevent mixture of cooling fluid within the conductive hollow tube 130 and gas within the volume 113. The proximal end 134 of the conductive hollow tube 130 is open to allow placement of the cooling tube 150, as well as flow of cooling fluid either in or out of the conductive hollow tube 130.

As best seen in FIG. 4, the cooling tube 150 has a distal end 152 and a proximal end 154. In the illustrated example, both the distal end 152 and the proximal end 154 are open to allow flow of a cooling fluid. For example, a cooling fluid may be introduced into the cooling tube 150 via the proximal end 154 of the cooling tube 150, flow through the distal end 153 of the cooling tube 150 into a distal portion of the conductive hollow tube 130, and flow out of the conductive hollow tube 130 via the proximal end 134 of the conductive hollow tube 130 along path 199. In other embodiments, the flow may be reversed from what is shown in FIG. 4.

Figure 5:
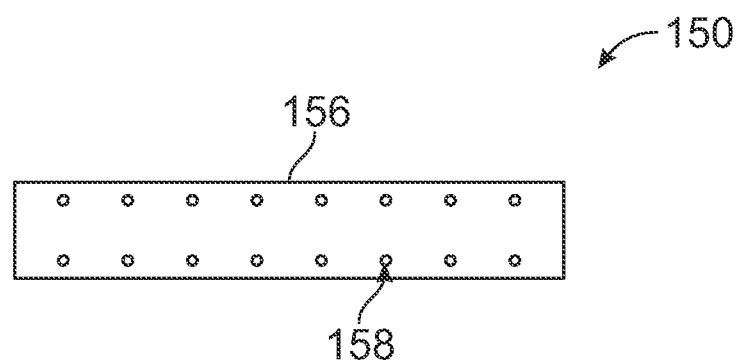
FIG. 5 illustrates a side view of a cooling tube, according to an embodiment of the present disclosure.

In other embodiments, the distal end 154 of the cooling tube 150 may be closed. For example, FIG. 5 provides a side view of an example cooling tube 150 that has a closed end. The depicted example cooling tube 150 of FIG. 5 includes a cooling sleeve 156. The cooling sleeve 156 defines the body of the cooling tube 150 and includes coolant openings 158 that pass through the cooling sleeve 156. The coolant openings allow a cooling fluid to pass from the interior of the cooling tube 150 into a space defined between the cooling tube and the interior surface of the hollow conductive tube 130.

With continued reference to FIGS. 1 and 2, in the illustrated example, the excimer lamp 100 includes a spacer 190 that fits around the exterior surface 133 of the conductive hollow tube 130, and within the interior surface 116 of the dielectric tube. The depicted spacer 190 is an annular ring (or doughnut-shaped) to match the cross-sections of the dielectric tube 110 and the conductive hollow tube 130. The spacer, which may be made of Teflon, for example, helps position and support the conductive hollow tube 130 inside the dielectric tube 110.

The electrode grid 140 is disposed on the exterior surface 118 of the dielectric tube 110, with the body of the dielectric tube 110 and gas within the volume 113 interposed between the electrode grid 140 and the conductive hollow tube 130. The conductive hollow tube 130 and electrode grid 140 are coupled to an electrical supply and act as the electrodes used to cause the gas in the volume 113 to emit UV light. In the illustrated embodiment, the electrode grid 140 is coupled to ground conductor 160, and the conductive hollow tube 130 is coupled to a positive conductor 162.

The electrode grid 140 may be integral with or formed with or applied on the dielectric tube 110, or may be a separate physical component in various embodiments. For example, in some embodiments, the electrode grid 140 includes printed wires 144 (only a portion of the printed wires 144 are shown in FIG. 1 for ease of depicting internal portions of the excimer lamp 100) that are applied to the exterior surface 118 of the dielectric tube 110.

Figure 6:
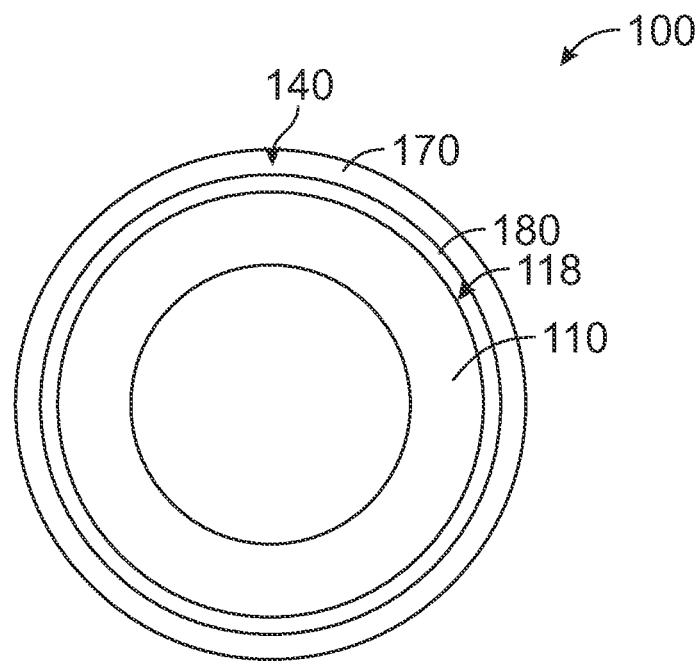
FIG. 6 illustrates an end sectional view of an alternate embodiment of the excimer lamp of FIG. 1.

As another example, a separate physical structure may be used to provide the electrode grid 140. For instance, FIG. 6 provides an end view of an example excimer lamp 100 that includes an electrode grid 140 that includes a sleeve 170. The sleeve 170 fits around the dielectric tube 110 to position the electrode grid 140 proximal the exterior surface 118 of the dielectric tube 110. In the illustrated example, the excimer lamp 100 of FIG. 6 includes a band pass filter 180 that is disposed proximate the electrode grid 140 and acts to limit the wavelengths emitted by the excimer lamp 100. In some embodiments, for example, the band pass filter 180 may be printed or otherwise formed on the exterior surface 118 of the dielectric tube 110 before the sleeve 170 is placed in position.

Figure 7:
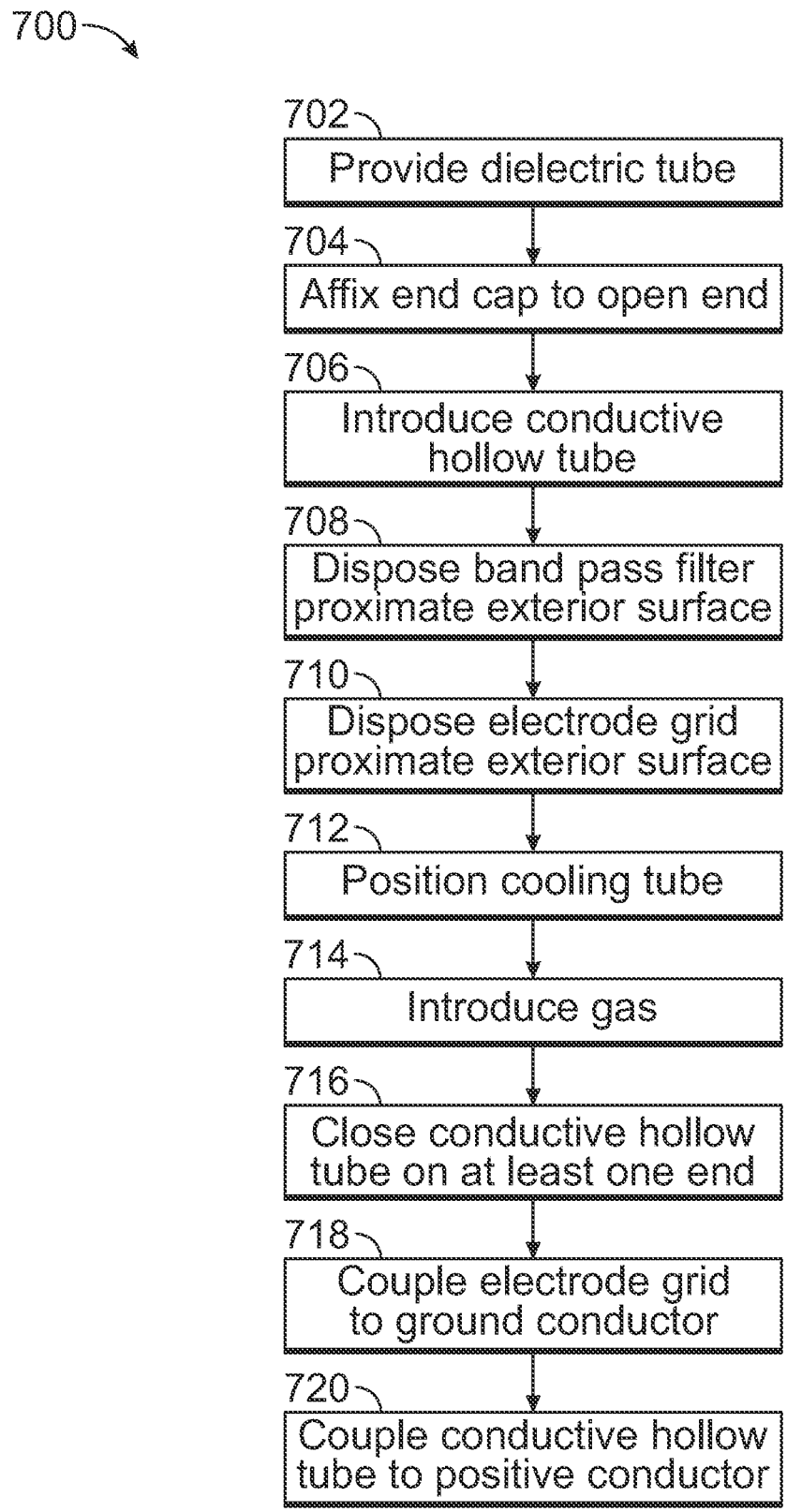
FIG. 7 illustrates a flowchart of a method, according to an embodiment of the present disclosure.

FIG. 7 provides a flowchart of a method 700 for assembling an excimer lamp (e.g., excimer lamp 100). The method 700 in various embodiments utilizes and/or provides one or more aspects discussed above in connection with the example excimer lamps 100 discussed herein. It may be noted that steps may be added or omitted in various embodiments, and/or various steps may be performed in a different order than shown in FIG. 7.

At 702, a dielectric tube (e.g., dielectric tube 110) is provided. The dielectric tube has a closed end and an open end, and defines a cavity. The dielectric tube, for example, may be formed of quartz glass or other transparent, dielectric material.

At 704, an end cap (e.g., end cap 120) is affixed to the open end of the dielectric tube. The end cap, for example, may be brazed to the dielectric tube to provide a seal.

At 706, a conductive hollow tube (e.g., conductive hollow tube 130) is introduced into the cavity. The conductive hollow tube passes through the end cap and into the cavity of the dielectric tube. For example, the conductive hollow tube may be inserted through an opening of the end cap, and brazed to the end cap to provide a seal once the conductive hollow tube is in a desired position. In some embodiments, a spacer (e.g., spacer 190) is used to position and/or support the conductive hollow tube. After the conductive hollow tube is positioned in the cavity, a volume is defined between an exterior surface of the conductive hollow tube and an interior surface of the dielectric tube. The volume is used to hold gas during operation of the excimer lamp.

At 708 of the illustrated example, a band pass filter (e.g., band pass filter 180) is disposed proximate the exterior surface of the dielectric tube. For example, the band pass filter may be printed on the exterior surface.

At 710, an electrode grid (e.g., electrode grid 140) is disposed proximate (e.g., on) the exterior surface of the dielectric tube. The electrode grid may be provided by printing wires on the exterior surface, or, as another example, may be provided by positioning a sleeve around at least portion of the exterior surface of the dielectric tube. For example, in embodiments utilizing a band pass filter, the band pass filter may be printed on the exterior surface and then a sleeve containing the electrode grid may be positioned over the exterior surface.

Cooling of the excimer lamp may be provided in some embodiments. For example, in some embodiments, at 712, a cooling tube (e.g., cooling tube 150) is positioned within the conductive hollow tube.

At 714, a gas (e.g., Krypton Chlorine gas) is introduced into the volume. For example, the gas may be introduced into the volume via the conductive hollow tube.

At 716, the conductive hollow tube is closed on at least one end. For example, after filling the cavity with gas, the proximal end of the conductive hollow tube may be closed to provide a seal to maintain the gas in the cavity of the dielectric tube. In embodiments using a cooling tube, the conductive hollow tube may have a closed distal end, and the gas introduced with a separate fill tube which is crimped or otherwise sealed after a desired amount of gas is in the cavity.

The electrode grid and conductive hollow tube may next be coupled to an electrical source. In the illustrated example, at 718, the electrode grid is coupled to a ground conductor, and at 720, the conductive hollow tube is coupled to a positive conductor. A voltage may be applied to the conductive hollow tube and electrode grid which act as electrodes of the excimer lamp, causing the gas to emit UV light.

Figure 8:
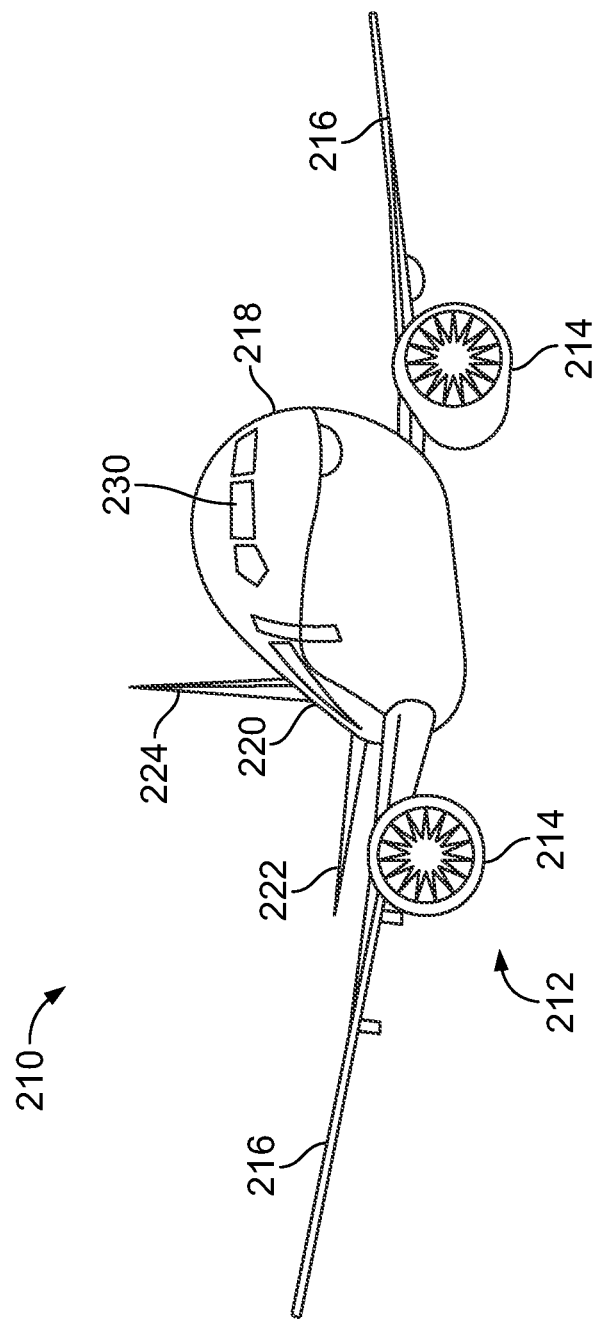
FIG. 8 illustrates a perspective front view of an aircraft, according to an embodiment of the present disclosure.

FIG. 8 illustrates a perspective front view of an aircraft 210, according to an embodiment of the present disclosure. The aircraft 210 includes a propulsion system 212 that includes engines 214, for example. Optionally, the propulsion system 212 may include more engines 14 than shown. The engines 214 are carried by wings 216 of the aircraft 210. In other embodiments, the engines 214 may be carried by a fuselage 218 and/or an empennage 220. The empennage 220 may also support horizontal stabilizers 222 and a vertical stabilizer 224.

The fuselage 218 of the aircraft 210 defines an internal cabin 230, which includes a flight deck or cockpit, one or more work sections (for example, galleys, personnel carry-on baggage areas, and the like), one or more passenger sections (for example, first class, business class, and coach sections), one or more lavatories, and/or the like. The internal cabin 230 includes one or more lavatory systems, lavatory units, or lavatories, as described herein.

Alternatively, instead of an aircraft, embodiments of the present disclosure may be used with various other vehicles, such as automobiles, buses, locomotives and train cars, watercraft, and the like. Further, embodiments of the present disclosure may be used with respect to fixed structures, such as commercial and residential buildings.

Figure 9A:
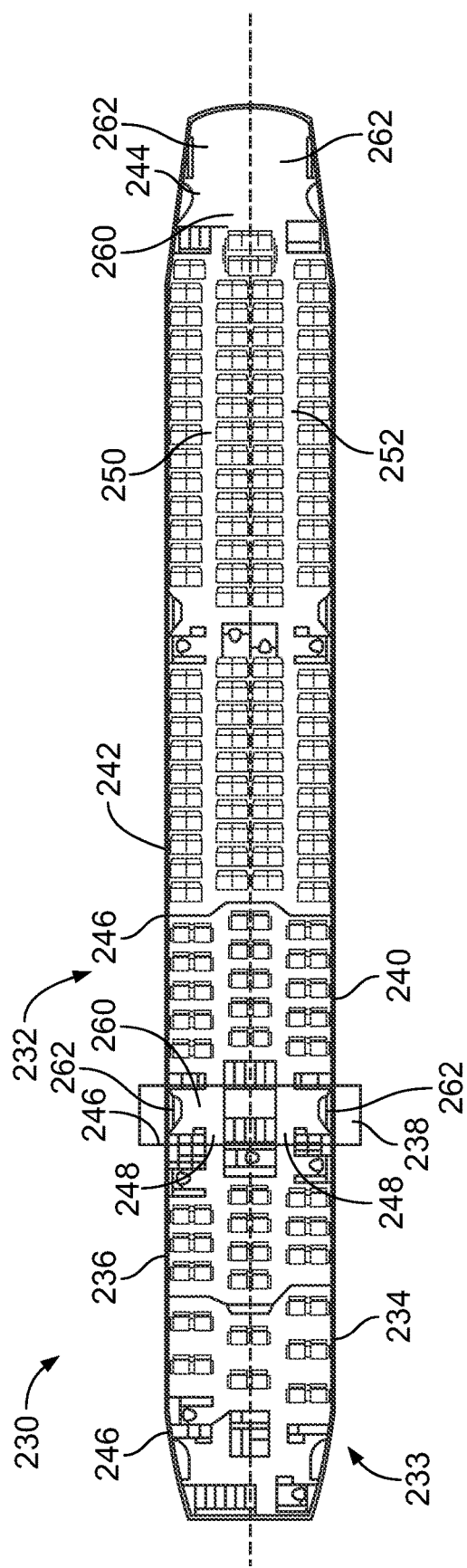
FIG. 9A illustrates a top plan view of an internal cabin of an aircraft, according to an embodiment of the present disclosure.

FIG. 9A illustrates a top plan view of an internal cabin 230 of an aircraft, according to an embodiment of the present disclosure. The internal cabin 230 may be within the fuselage 232 of the aircraft, such as the fuselage 218 of FIG. 8. For example, one or more fuselage walls may define the internal cabin 230. The internal cabin 230 includes multiple sections, including a front section 233, a first class section 234, a business class section 236, a front galley station 238, an expanded economy or coach section 240, a standard economy of coach section 242, and an aft section 244, which may include multiple lavatories and galley stations. It is to be understood that the internal cabin 230 may include more or less sections than shown. For example, the internal cabin 230 may not include a first class section, and may include more or less galley stations than shown. Each of the sections may be separated by a cabin transition area 246, which may include class divider assemblies between aisles 248.

As shown in FIG. 9A, the internal cabin 230 includes two aisles 250 and 252 that lead to the aft section 244. Optionally, the internal cabin 230 may have less or more aisles than shown. For example, the internal cabin 230 may include a single aisle that extends through the center of the internal cabin 230 that leads to the aft section 244.

The aisles 248, 250, and 252 extend to egress paths or door passageways 260. Exit doors 262 are located at ends of the egress paths 260. The egress paths 260 may be perpendicular to the aisles 248, 250, and 252. The internal cabin 230 may include more egress paths 260 at different locations than shown. The portable sanitizing system 100 shown and described with respect to FIGS. 1-18 may be used to sanitize various structures within the internal cabin 230, such as passenger seats, monuments, stowage bin assemblies, components on and within lavatories, galley equipment and components, and/or the like.

Figure 9B:
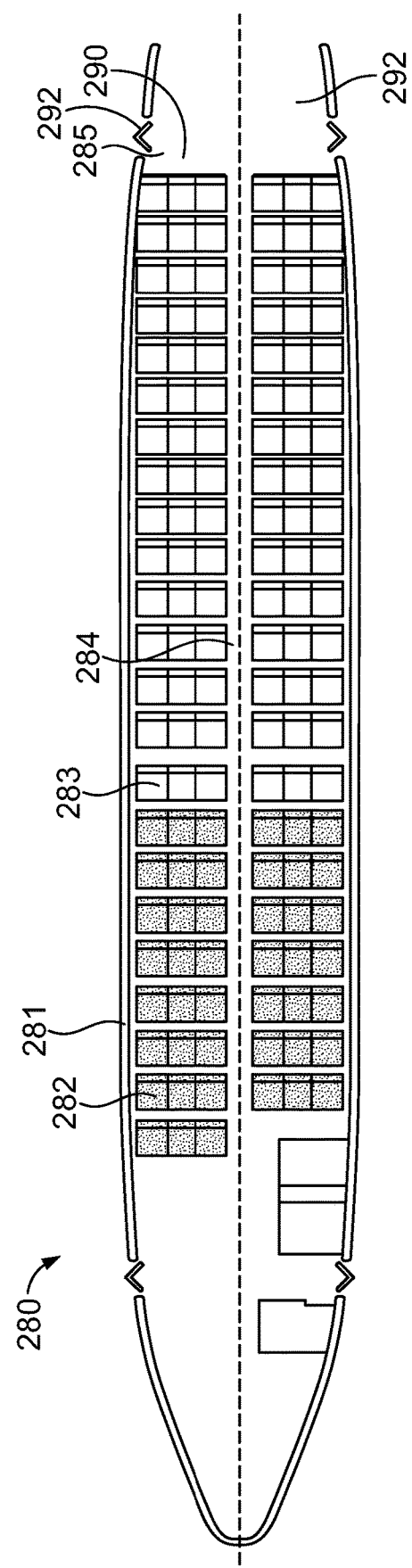
FIG. 9B illustrates a top plan view of an internal cabin of an aircraft, according to an embodiment of the present disclosure.

FIG. 9B illustrates a top plan view of an internal cabin 280 of an aircraft, according to an embodiment of the present disclosure. The internal cabin 280 is an example of the internal cabin 230 shown in FIG. 8. The internal cabin 280 may be within a fuselage 281 of the aircraft. For example, one or more fuselage walls may define the internal cabin 280. The internal cabin 280 includes multiple sections, including a main cabin 282 having passenger seats 283, and an aft section 285 behind the main cabin 282. It is to be understood that the internal cabin 280 may include more or less sections than shown.

The internal cabin 280 may include a single aisle 284 that leads to the aft section 285. The single aisle 284 may extend through the center of the internal cabin 280 that leads to the aft section 285. For example, the single aisle 284 may be coaxially aligned with a central longitudinal plane of the internal cabin 280.

The aisle 284 extends to an egress path or door passageway 290. Exit doors 292 are located at ends of the egress path 290. The egress path 290 may be perpendicular to the aisle 284. The internal cabin 280 may include more egress paths than shown. The portable sanitizing system 100 shown and described with respect to FIGS. 1-18 may be used to sanitize various structures within the internal cabin 230, such as passenger seats, monuments, stowage bin assemblies, components on and within lavatories, galley equipment and components, and/or the like.

Figure 10:
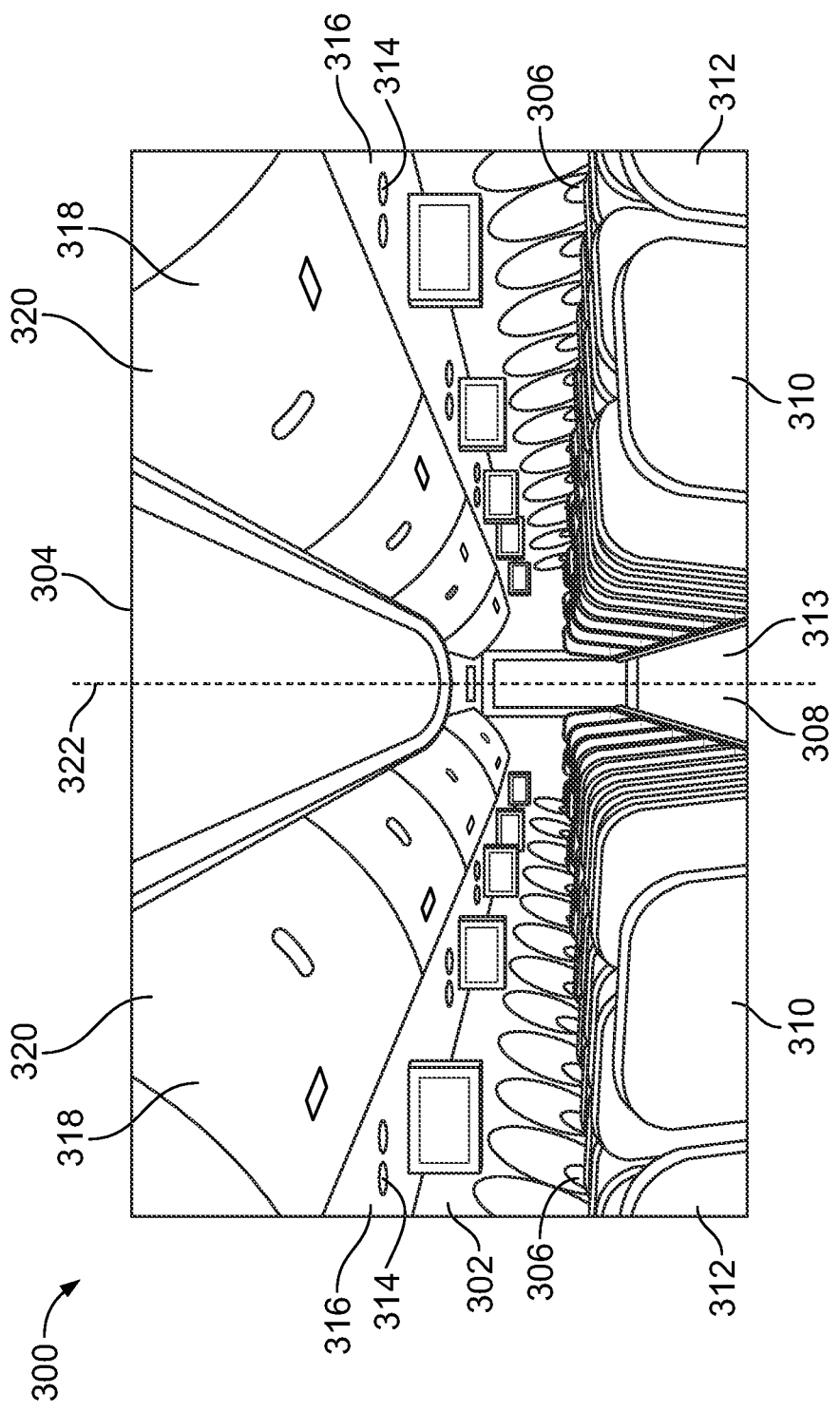
FIG. 10 illustrates a perspective interior view of an internal cabin of an aircraft, according to an embodiment of the present disclosure.

FIG. 10 illustrates a perspective interior view of an internal cabin 300 of an aircraft, according to an embodiment of the present disclosure. The internal cabin 300 includes outboard walls 302 connected to a ceiling 304. Windows 306 may be formed within the outboard walls 302. A floor 308 supports rows of seats 310. As shown in FIG. 10, a row 312 may include two seats 310 on either side of an aisle 313. However, the row 312 may include more or less seats 310 than shown. Additionally, the internal cabin 300 may include more aisles than shown.

Passenger service units (PSUs) 314 are secured between an outboard wall 302 and the ceiling 304 on either side of the aisle 313. The PSUs 314 extend between a front end and rear end of the internal cabin 300. For example, a PSU 314 may be positioned over each seat 310 within a row 312. Each PSU 314 may include a housing 316 that generally contains vents, reading lights, an oxygen bag drop panel, an attendant request button, and other such controls over each seat 310 (or groups of seats) within a row 312.

Overhead stowage bin assemblies 318 are secured to the ceiling 304 and/or the outboard wall 302 above and inboard from the PSU 314 on either side of the aisle 313. The overhead stowage bin assemblies 318 are secured over the seats 310. The overhead stowage bin assemblies 318 extend between the front and rear end of the internal cabin 300. Each stowage bin assembly 318 may include a pivot bin or bucket 320 pivotally secured to a strongback (hidden from view in FIG. 10). The overhead stowage bin assemblies 318 may be positioned above and inboard from lower surfaces of the PSUs 314. The overhead stowage bin assemblies 318 are configured to be pivoted open in order to receive passenger carry-on baggage and personal items, for example.

As used herein, the term "outboard" means a position that is further away from a central longitudinal plane 322 of the internal cabin 300 as compared to another component. The term "inboard" means a position that is closer to the central longitudinal plane 322 of the internal cabin 300 as compared to another component. For example, a lower surface of a PSU 314 may be outboard in relation to a stowage bin assembly 318.

The excimer lamps discussed herein may be used to sanitize various structures shown within the internal cabin 300.

Figure 11:
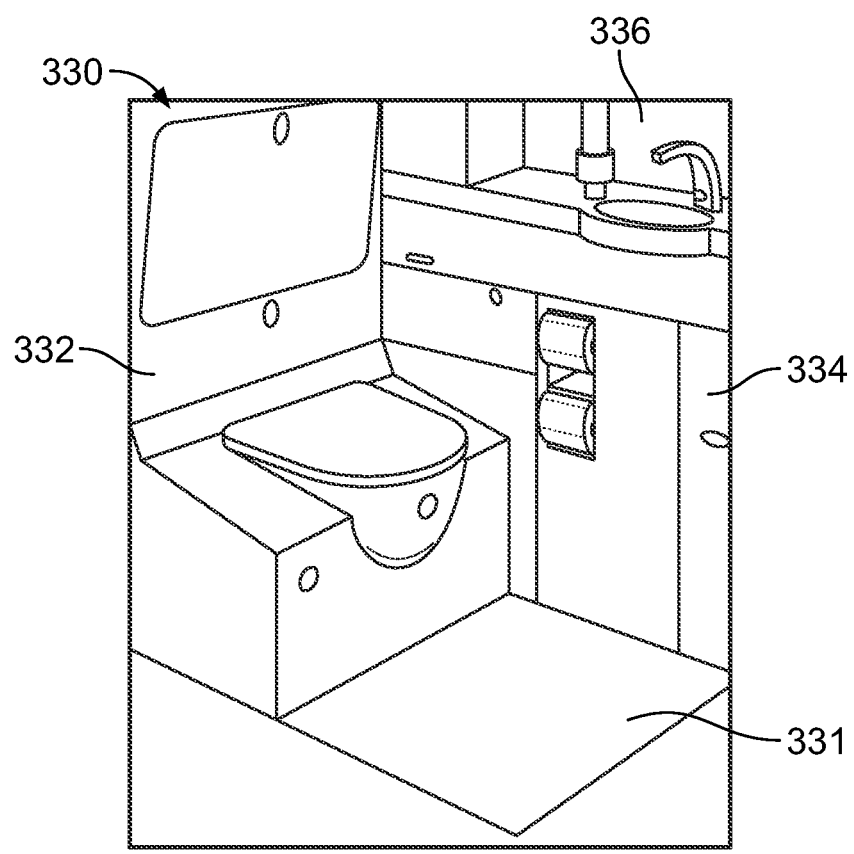
FIG. 11 illustrates a perspective internal view of a lavatory within an internal cabin of an aircraft.

FIG. 11 illustrates a perspective internal view of a lavatory 330 within an internal cabin of a vehicle, such as any of the internal cabins described herein. The lavatory 330 is an example of an enclosed space, monument or chamber, such as within the internal cabin a vehicle. The lavatory 330 may be onboard an aircraft, as described above. Optionally, the lavatory 330 may be onboard various other vehicles. In other embodiments, the lavatory 330 may be within a fixed structure, such as a commercial or residential building. The lavatory 330 includes a base floor 331 that supports a toilet 332, cabinets 334, and a sink 336 or wash basin. The lavatory 330 may be arranged differently than shown. The lavatory 330 may include more or less components than shown. The excimer lamps discussed herein may be used to sanitize the various structures, components, and surfaces within the lavatory 330.

Further, the disclosure comprises embodiments according to the following clauses:

Clause 1. An excimer lamp comprising:
a dielectric tube having a closed end and an open end, the dielectric tube defining a cavity;
an end cap sealingly covering the open end;
a conductive hollow tube passing through the end cap and into the cavity of the dielectric tube, a volume defined between an exterior surface of the conductive hollow tube and an interior surface of the dielectric tube, the volume configured to hold a gas; and
an electrode grid disposed on an exterior surface of the dielectric tube.

Clause 2. The excimer lamp of Clause 1, wherein the dielectric tube is made of a quartz material.

Clause 3. The excimer lamp of Clause 1 or 2, wherein the end cap is brazed to the dielectric tube.

Clause 4. The excimer lamp of any of Clauses 1-3, wherein the end cap has a thermal coefficient of expansion that corresponds to a thermal coefficient of expansion of the dielectric tube.

Clause 5. The excimer lamp of any of Clauses 1-4, wherein the conductive hollow tube is made of stainless steel.

Clause 6. The excimer lamp of any of Clauses 1-5, wherein the conductive hollow tube is closed on at least one end.

Clause 7. The excimer lamp of Clause 6, wherein the conductive hollow tube comprises a sleeve that comprises circulation holes passing through the sleeve.

Clause 8. The excimer lamp of Clause 7, wherein the conductive hollow tube is configured to allow passage of a cooling fluid.

Clause 9. The excimer lamp of Clause 8, further comprising a cooling tube disposed within the conductive hollow tube.

Clause 10. The excimer lamp of Clause 9, wherein the cooling tube has an open distal end.

Clause 11. The excimer lamp of Clause 9, wherein the cooling tube comprises a cooling sleeve, the cooling sleeve comprising coolant openings passing through the cooling sleeve.

Clause 12. The excimer lamp of any of Clauses 1-11, wherein the electrode grid is coupled to a ground conductor, and the conductive hollow tube is coupled to a positive conductor.

Clause 13. The excimer lamp of any of Clauses 1-12, wherein the electrode grid comprises printed wires applied to the exterior surface of the dielectric tube.

Clause 14. The excimer lamp of any of Clauses 1-13, wherein the electrode grid comprises a sleeve disposed around at least a portion of the exterior surface of the dielectric tube.

Clause 15. The excimer lamp of any of Clauses 1-14, further comprising a band pass filter disposed proximate the electrode grid.

Clause 16. A method for providing an excimer lamp comprising:
providing a dielectric tube having a closed end and an open end, the dielectric tube defining a cavity;
affixing an end cap to cover the open end;
introducing a conductive hollow tube into the cavity, the conductive hollow tube passing through the end cap and into the cavity of the dielectric tube, a volume defined between an exterior surface of the conductive hollow tube and an interior surface of the dielectric tube;
disposing an electrode grid on an exterior surface of the dielectric tube; and
introducing a gas into the volume.

Clause 17. The method of Clause 16, wherein the gas is introduced into the volume via the conductive hollow tube.

Clause 18. The method of Clause 16 of 17, further comprising closing the conductive hollow tube on at least one end.

Clause 19. The method of any of Clauses 16-18, further comprising positioning a cooling tube within the conductive hollow tube.

Clause 20. The method of any of Clauses 16-19, further comprising:
coupling the electrode grid to a ground conductor; and
coupling the conductive hollow tube to a positive conductor.

Clause 21. The method of any of Clauses 16-20, wherein disposing the electrode grid on the exterior surface of the dielectric tube comprises printing wires on the exterior surface of the dielectric tube.

Clause 22. The method of any of Clauses 16-21, wherein disposing the electrode grid on the exterior surface of the dielectric tube comprises positioning a sleeve around at least a portion of the exterior surface of the dielectric tube.

Clause 23. The method of any of Clauses 16-22, further comprising disposing a band pass filter proximate the exterior surface of the dielectric tube While various spatial and directional terms, such as top, bottom, lower, mid, lateral, horizontal, vertical, front and the like can be used to describe embodiments of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. An excimer lamp comprising:
   a dielectric tube having a closed end and an open end, the dielectric tube defining a cavity;
   an end cap sealingly covering the open end;
   a conductive hollow tube passing through the end cap and into the cavity of the dielectric tube, a volume defined between an exterior surface of the conductive hollow tube and an interior surface of the dielectric tube, the volume configured to hold a gas; and
   an electrode grid disposed on an exterior surface of the dielectric tube.

2. The excimer lamp of claim 1, wherein the dielectric tube is made of a quartz material.

3. The excimer lamp of claim 1, wherein the end cap is brazed to the dielectric tube.

4. The excimer lamp of claim 1, wherein the end cap has a thermal coefficient of expansion that corresponds to a thermal coefficient of expansion of the dielectric tube.

5. The excimer lamp of claim 1, wherein the conductive hollow tube is made of stainless steel.

6. The excimer lamp of claim 1, wherein the conductive hollow tube is closed on at least one end.

7. The excimer lamp of claim 6, wherein the conductive hollow tube comprises a sleeve that comprises circulation holes passing through the sleeve.

8. The excimer lamp of claim 7, wherein the conductive hollow tube is configured to allow passage of a cooling fluid.

9. The excimer lamp of claim 8, further comprising a cooling tube disposed within the conductive hollow tube.

10. The excimer lamp of claim 9, wherein the cooling tube has an open distal end.

11. The excimer lamp of claim 9, wherein the cooling tube comprises a cooling sleeve, the cooling sleeve comprising coolant openings passing through the cooling sleeve.

12. The excimer lamp of claim 1, wherein the electrode grid is coupled to a ground conductor, and the conductive hollow tube is coupled to a positive conductor.

13. The excimer lamp of claim 1, wherein the electrode grid comprises printed wires applied to the exterior surface of the dielectric tube.

14. The excimer lamp of claim 1, wherein the electrode grid comprises a sleeve disposed around at least a portion of the exterior surface of the dielectric tube.

15. The excimer lamp of claim 1, further comprising a band pass filter disposed proximate the electrode grid.

16. A method for providing an excimer lamp comprising:
   providing a dielectric tube having a closed end and an open end, the dielectric tube defining a cavity;
   affixing an end cap to cover the open end;
   introducing a conductive hollow tube into the cavity, the conductive hollow tube passing through the end cap and into the cavity of the dielectric tube, a volume defined between an exterior surface of the conductive hollow tube and an interior surface of the dielectric tube;
   disposing an electrode grid on an exterior surface of the dielectric tube; and
   introducing a gas into the volume.

17. The method of claim 16, wherein the gas is introduced into the volume via the conductive hollow tube.

18. The method of claim 16, further comprising closing the conductive hollow tube on at least one end.

19. The method of claim 16, further comprising positioning a cooling tube within the conductive hollow tube.

20. The method of claim 16, further comprising:
   coupling the electrode grid to a ground conductor; and
   coupling the conductive hollow tube to a positive conductor.

* * * * *